US00PP36121P2

(12) United States Plant Patent
van der Lugt

(10) Patent No.: US PP36,121 P2
(45) Date of Patent: Sep. 17, 2024

(54) ***EUPHORBIA* PLANT NAMED 'Bonpr 974BK'**

(50) Latin Name: ***Euphorbia pulcherrima* Willd. ex *Klotzsch* X *Euphorbia cornastra***
Varietal Denomination: Bonpr 974BK

(71) Applicant: Ard van der Lugt, Maasdijk (NL)

(72) Inventor: Ard van der Lugt, Maasdijk (NL)

(73) Assignee: BONZA BOTANICALS PTY., LTD., Yellow Rock (AU)

( * ) Notice: Subject to any disclaimer, the term of this patent is extended or adjusted under 35 U.S.C. 154(b) by 0 days.

(21) Appl. No.: 18/419,530

(22) Filed: Jan. 22, 2024

(51) Int. Cl.
*A01H 5/02* (2018.01)
*A01H 6/38* (2018.01)

(52) U.S. Cl.
USPC ..... Plt./304

(58) Field of Classification Search
USPC ..... Plt./263.1, 302, 304
See application file for complete search history.

(56) References Cited

U.S. PATENT DOCUMENTS

PP25,116 P2 * 11/2014 Bernuetz ..... A01H 6/385
Plt./304

* cited by examiner

*Primary Examiner* — Karen M Redden
(74) *Attorney, Agent, or Firm* — C. Anne Whealy

(57) ABSTRACT

A new and distinct cultivar of *Euphorbia* plant named 'Bonpr 974BK', characterized by its upright and mounded plant habit; moderately vigorous growth habit; freely branching habit; large inflorescences with white-colored flower bracts; and good post-production longevity.

2 Drawing Sheets

Figure 1:
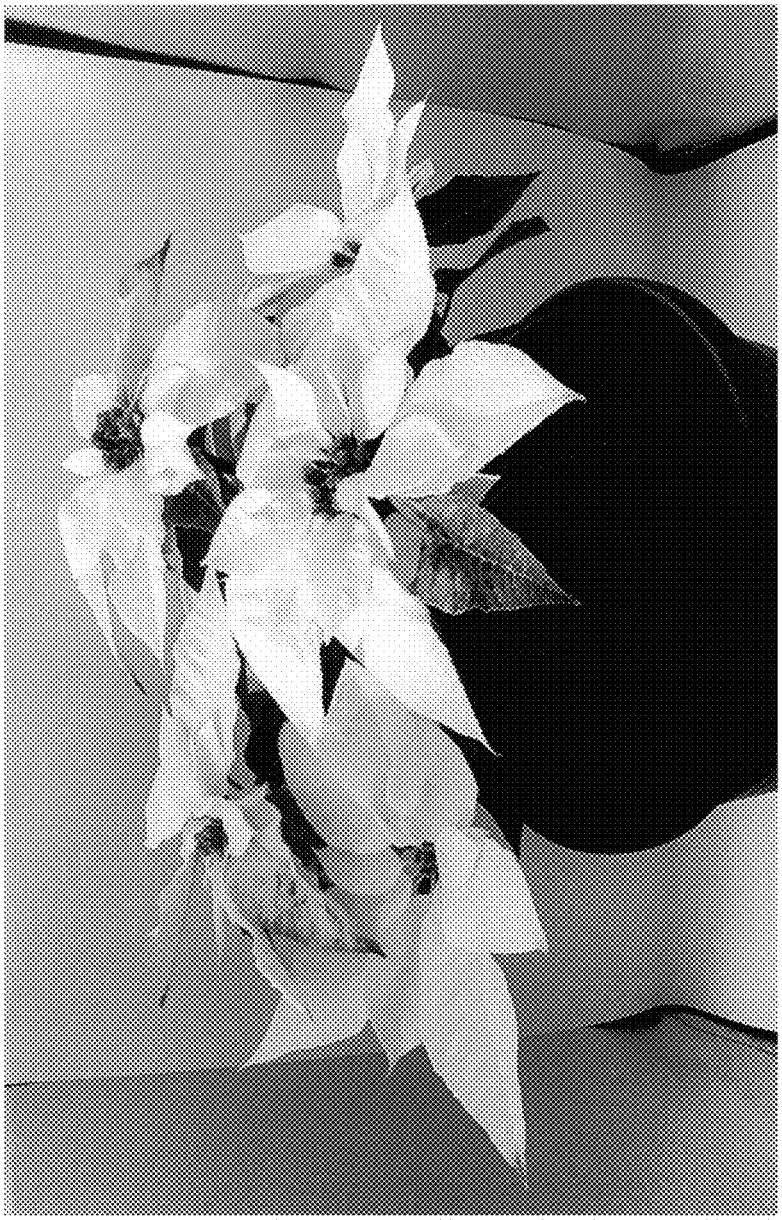

Botanical designation: *Euphorbia pulcherrima* Willd. ex *Klotzsch* X *Euphorbia cornastra,*
Cultivar denomination: 'BONPR 974BK'.

BACKGROUND OF THE INVENTION

The present invention relates to a new and distinct cultivar of *Euphorbia* plant, an interspecific hybrid botanically known as *Euphorbia pulcherrima*Willd. ex *Klotzsch* X *Euphorbia cornastra*, and hereinafter referred to by the cultivar name 'Bonpr 974BK'.

The new *Euphorbia* plant is a naturally-occurring whole plant mutation of *Euphorbia pulcherrima* Willd. ex *Klotzsch* X *Euphorbia cornastra* 'Bonpri 974', disclosed in U.S. Plant Pat. No. 27,689. The new *Euphorbia* plant was discovered and selected by the Inventor as a single flowering plant from within a population of plants of 'Bonpri 974' in a controlled greenhouse environment in Maasdijk, The Netherlands in November, 2019.

Asexual reproduction of the new *Euphorbia* plant by terminal vegetative cuttings in a controlled greenhouse environment in Maasdijk, The Netherlands since August, 2020 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bonpr 974BK'. These characteristics in combination distinguish 'Bonpr 974BK' as a new and distinct *Euphorbia* plant:

1. Upright and mounded plant habit.
2. Moderately vigorous growth habit.
3. Freely branching habit.
4. Large inflorescences with white-colored flower bracts.
5. Good post-production longevity.

Plants of the new *Euphorbia* differ primarily from plants of the mutation parent, Bonpri 974' in plant and growth habit. Plants of the new *Euphorbia* flower are larger and more vigorous than and not as compact as plants of 'Bonpri 974'. In addition, plants of the new *Euphorbia* have larger leaves than plants of 'Bonpri 974'.

Plants of the new *Euphorbia* can be compared to plants of the *Euphorbia pulcherrima* Willd. ex *Klotzsch* X *Euphorbia cornastra* 'Bonpri 635', disclosed in U.S. Plant Pat. No. 25,116. In side-by-side comparisons, plants of the new *Euphorbia* differ primarily from plants of 'Bonpri 635' in the following characteristics:

1. Plants of the new *Euphorbia* are taller than plants of 'Bonpri 635'.
2. Plants of the new *Euphorbia* have larger flower bracts than plants of 'Bonpri 635'.
3. Plants of the new *Euphorbia* and 'Bonpri 635' differ in flower bract color as flower bracts of plants of the new *Euphorbia* are white in color whereas flower bracts of plants of 'Bonpri 635' are white in color with red purple-colored venation and occasional random spots.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph on the first sheet (FIG. 1) is a side perspective view of a typical flowering plant of 'Bonpr 974BK' grown in a container.

Figure 2:
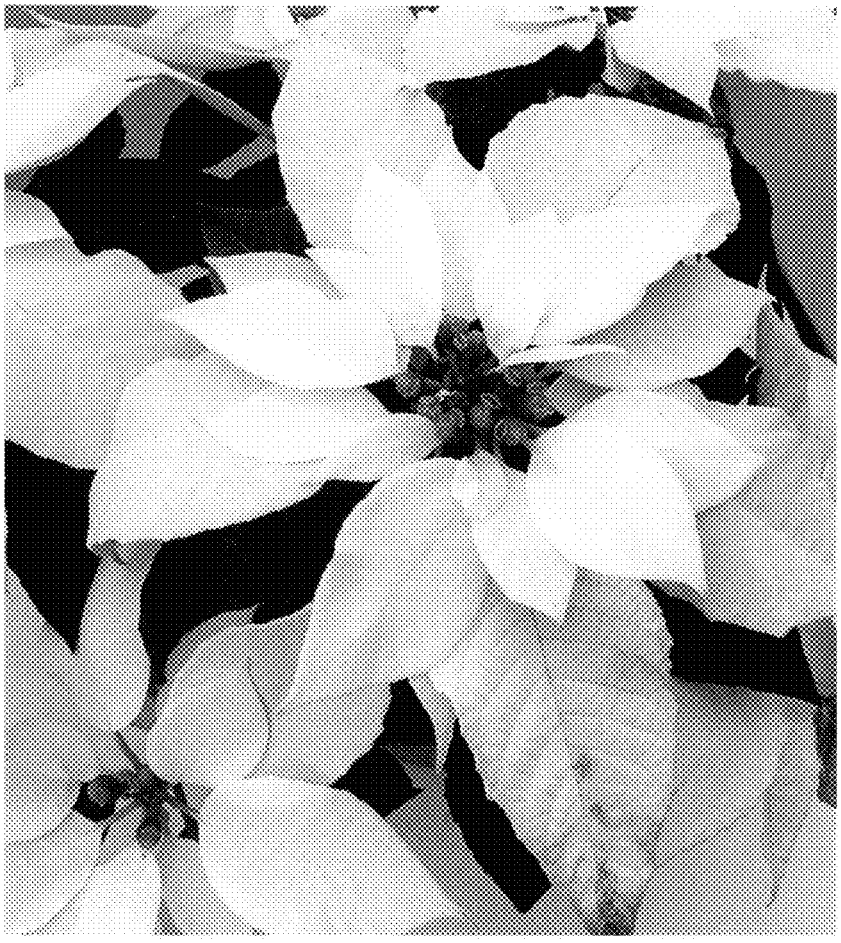

The photograph on the second sheet (FIG. 2) is a close-up view of a typical flowering plant of 'Bonpr 974BK'.

DETAILED BOTANICAL DESCRIPTION

Plants used in the aforementioned photographs and described herewith in detail were grown during the autumn and early winter in 10.5-cm containers in an outdoor nursery in Higashiomi, Shiga, Japan and under cultural practices typical of commercial *Euphorbia* production. During the production of the plants, day temperatures averaged 23° C. and night temperatures averaged 13° C. Plants were six months old when the photographs and the description were taken. In the following description, color references are made to The Royal Horticultural Society Colour Chart, 2015 Edition, except where general terms of ordinary dictionary significance are used.

Botanical classification: *Euphorbia pulcherrima* Willd. ex *Klotzsch* X *Euphorbia cornastra* 'Bonpr 974BK'.

Parentage: Naturally-occurring whole plant mutation of *Euphorbia pulcherrima* Willd. ex *Klotzsch* X *Euphorbia cornastra* 'Bonpri 974', disclosed in U.S. Plant Pat. No. 27,689.

Propagation:

*Type*.—Terminal vegetative cuttings.

*Time to initiate roots, summer*.—About ten days at temperatures about 20° C. to 21° C.

*Time to initiate roots, winter*.—About twelve days at temperatures about 20° C. to 21° C.

*Time to produce a rooted young plant, summer*.—About 24 days at temperatures about 20° C. to 21° C.

*Time to produce a rooted young plant, winter*.—About 28 days at temperatures about 20° C. to 21° C.

*Root description*.—Fibrous; typically white in color, actual color of the roots is dependent on substrate composition, water quality, fertilizers, substrate temperature and physiological age of roots.

*Rooting habit*.—Freely branching; medium density.

Plant description:

*Plant habit and form*.—Upright and mounded plant habit; inverted triangle; inflorescences positioned above the foliar plane; moderately vigorous growth habit.

*Plant height*.—About 28.5 cm.

*Plant diameter or spread*.—About 43.8 cm.

*Lateral branch description*.—Branching habit: Freely branching habit, about seven lateral branches develop per plant. Length: About 24 cm. Diameter: About 4.9 mm. Internode length: About 2.9 cm. Aspect: Mostly upright to somewhat outward. Strength: Moderately strong. Texture and luster: Smooth, glabrous; glossy. Color: Close to 144A.

*Leaf description*.—Arrangement: Alternate, simple. Length: About 8.7 cm. Width: About 4.7 cm. Shape: Lanceolate. Apex: Acute. Base: Rounded. Margin: Mostly entire, occasionally with few shallow lobes. Venation pattern: Pinnate, reticulate. Texture and luster, upper and lower surfaces: Smooth, glabrous; matte. Color: Developing and fully developed leaves, upper surface: Darker than NN137A; venation, close to 138A. Developing and fully developed leaves, lower surface: Close to NN137C; venation, close to 138A. Petioles: Length: About 2 cm. Diameter: About 2 mm. Texture, upper and lower surfaces: Sparsely pubescent. Color, upper and lower surfaces: Close to 144A.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—One per lateral branch, about eight inflorescences develop per plant.

*Inflorescence diameter*.—About 21.5 cm.

*Inflorescence height*.—About 5.5 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering response, plants flower about 49 to 50 days under natural season or photoinductive conditions in Japan.

*Post-production longevity*.—Good post-production longevity; plants of the new *Euphorbia* maintain good substance and bract color for about six to eight weeks.

*Flower bracts*.—Quantity per inflorescence: About 15. Length, largest bracts: About 9 cm. Width, largest bracts: About 4.7 cm. Aspect: Mostly horizontal and flat. Shape: Elliptic. Apex: Acute. Base: Obtuse. Margin: Entire. Texture and luster, upper and lower surfaces: Smooth, glabrous; matte. Venation pattern: Pinnate, reticulate. Color: Transitional bracts, upper surface: Random sectors, close to 157D and 143B. Transitional bracts, lower surface: Random sectors, close to NN155A and 143C. Developing and fully expanded bracts, upper surface: Close to 157D; venation, close to 157B; flower bract color does not change with subsequent development. Fully expanded bracts, lower surface: Close to 157D; venation, close to 157A; flower bract color does not change with subsequent development. Flower bract petioles: Length: About 1.6 cm. Diameter: About 1.9 mm. Texture, upper and lower surfaces: Smooth, glabrous. Color, upper and lower surfaces: Close to 157A.

*Cyathia*.—Quantity per corymb: About 13. Diameter of cyathia cluster: About 3.4 cm. Height, individual cyathium: About 5.9 mm. Diameter, individual cyathium: About 7.2 mm. Shape, individual cyathium: Globose. Color: Distally, close to 5C and proximally, close to 143C. Nectaries: Quantity per cyathium: About 13. Size: About 2.8 mm by 4.5 mm. Texture: Smooth, glabrous. Color: Close to 7A.

*Peduncles*.—Length: About 2.5 mm. Diameter: About 2.4 mm. Texture, upper and lower surfaces: Smooth, glabrous. Aspect: Mostly upright. Color, upper and lower surfaces: Close to 143C.

*Reproductive organs*.—Stamens: Quantity per cyathia: Two. Filament length: About 3 mm. Filament color: Close to 150C. Anther size: About 0.3 mm by 0.7 mm. Anther shape: Linear and globose. Anther color: Close to 154A. Pollen amount: If present, sparse. Pollen color: Close to 3C. Pistils: To date, pistil development has not been observed on plants of the new *Euphorbia*.

*Seeds and fruits*.—To date, seed and fruit development have not been observed on plants of the new *Euphorbia*.

Pathogen & pest resistance: To date, plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'Bonpr 974BK' as herein illustrated and described.

* * * * *